(12) United States Patent
Jeon

(10) Patent No.: US 12,082,873 B2
(45) Date of Patent: Sep. 10, 2024

(54) ENDOSCOPE HYBRID KNIFE

(71) Applicant: FINE MEDIX CO., LTD, Daegu (KR)

(72) Inventor: Seong Woo Jeon, Daegu (KR)

(73) Assignee: FINE MEDIX CO., LTD, Daegu (KR)

( * ) Notice: Subject to any disclaimer, the term of this patent is extended or adjusted under 35 U.S.C. 154(b) by 396 days.

(21) Appl. No.: 16/620,425

(22) PCT Filed: Apr. 12, 2018

(86) PCT No.: PCT/KR2018/004292
§ 371 (c)(1),
(2) Date: Dec. 6, 2019

(87) PCT Pub. No.: WO2018/230825
PCT Pub. Date: Dec. 20, 2018

(65) Prior Publication Data
US 2020/0390494 A1    Dec. 17, 2020

(30) Foreign Application Priority Data
Jun. 13, 2017    (KR) .......................... 10-2017-0074427

(51) Int. Cl.
*A61B 18/14*    (2006.01)
*A61B 18/00*    (2006.01)

(52) U.S. Cl.
CPC    *A61B 18/1492* (2013.01); *A61B 2018/00083* (2013.01); *A61B 2018/00166* (2013.01);
(Continued)

(58) Field of Classification Search
CPC ...... A61B 18/1492; A61B 2018/00083; A61B 2018/00601; A61B 2018/00946;
(Continued)

(56) References Cited

U.S. PATENT DOCUMENTS 5,114,399 A * 5/1992 Kovalcheck ... A61B 17/320758
606/159
5,486,183 A * 1/1996 Middleman ............ A61B 17/29
606/127

(Continued)

FOREIGN PATENT DOCUMENTS

JP    2001-079017 A    3/2001
JP    2009-240380 A    10/2009
(Continued)

*Primary Examiner* — Sean W Collins
(74) *Attorney, Agent, or Firm* — Bridgeway IP Law Group, PLLC; Jihun Kim

(57) ABSTRACT

An endoscope hybrid knife includes: a handle part having a hollow portion and an opening; first and second handle sliders coupled to the outer peripheral surface of the handle part so as to be slidable forwards and backwards in the longitudinal direction; a pipe disposed in the hollow portion of the handle part, and connected to the first handle slider; a second knife disposed to pass through the pipe, and connected to the second handle slider; a fluid injection part, which is coupled to one end of the handle part for injecting fluid therein; an inner tube which is connected to one end of the fluid injection part; a first knife coupled to the end of the pipe; and an insulating tip coupled to the end of the first knife, wherein the first knife and the second knife are slidable independently of each other.

16 Claims, 9 Drawing Sheets

(52) U.S. Cl.
CPC ........... *A61B 2018/00196* (2013.01); *A61B 2018/00482* (2013.01); *A61B 2018/00601* (2013.01); *A61B 2018/00946* (2013.01); *A61B 2018/00982* (2013.01); *A61B 2018/1405* (2013.01); *A61B 2018/1467* (2013.01); *A61B 2218/002* (2013.01)

(58) Field of Classification Search
CPC .. A61B 2018/00982; A61B 2018/1405; A61B 2218/002; A61B 18/00; A61B 18/14; A61L 31/04; A61L 31/048; Y10T 74/20468; B26B 1/00; B26B 5/001; B26B 13/00; A61N 1/00
See application file for complete search history.

(56) References Cited

U.S. PATENT DOCUMENTS

| | | | | |
|---|---|---|---|---|
| 5,527,327 | A * | 6/1996 | Louw | A61B 17/32075 606/159 |
| 5,536,248 | A * | 7/1996 | Weaver | A61M 25/0026 604/528 |
| 5,549,623 | A * | 8/1996 | Sharpe | A61B 17/3201 606/174 |
| 5,599,300 | A * | 2/1997 | Weaver | A61B 18/1492 128/898 |
| 5,601,572 | A * | 2/1997 | Middleman | A61B 18/082 606/139 |
| 5,720,754 | A * | 2/1998 | Middleman | A61B 18/082 606/127 |
| 7,150,747 | B1 * | 12/2006 | McDonald | A61B 18/148 606/49 |
| 2001/0020167 | A1 * | 9/2001 | Woloszko | A61B 18/149 606/49 |
| 2001/0053873 | A1 * | 12/2001 | Schaaf | A61F 9/00781 600/166 |
| 2003/0065326 | A1 * | 4/2003 | Wellman | A61B 18/1482 606/50 |
| 2003/0083684 | A1 * | 5/2003 | Cesarini | A61B 17/32002 606/171 |
| 2003/0236535 | A1 * | 12/2003 | Onuki | A61B 17/0482 606/144 |
| 2004/0059280 | A1 * | 3/2004 | Makower | A61B 17/3417 606/108 |
| 2004/0167514 | A1 * | 8/2004 | Okada | A61B 18/1492 606/45 |
| 2004/0210215 | A1 * | 10/2004 | Okada | A61B 18/1402 606/45 |
| 2004/0210284 | A1 * | 10/2004 | Okada | A61B 18/1402 607/96 |
| 2005/0072280 | A1 * | 4/2005 | Ono | A61B 18/1402 83/13 |
| 2005/0080320 | A1 * | 4/2005 | Lee | A61B 17/0293 600/214 |
| 2005/0096645 | A1 * | 5/2005 | Wellman | A61B 17/320016 606/171 |
| 2005/0096646 | A1 * | 5/2005 | Wellman | A61B 17/22031 606/171 |
| 2005/0096670 | A1 * | 5/2005 | Wellman | A61B 17/0218 606/139 |
| 2005/0096671 | A1 * | 5/2005 | Wellman | A61B 17/00008 606/139 |
| 2005/0216019 | A1 * | 9/2005 | Eckman | A61B 17/320016 606/79 |
| 2006/0173474 | A1 * | 8/2006 | Wellman | A61B 18/148 606/159 |
| 2006/0259070 | A1 * | 11/2006 | Livneh | A61B 17/2909 606/205 |
| 2006/0271079 | A1 * | 11/2006 | Akiba | A61B 18/1492 606/167 |
| 2006/0276784 | A1 * | 12/2006 | Miyajima | A61B 18/1492 606/46 |
| 2007/0135822 | A1 * | 6/2007 | Onuki | A61B 17/0469 606/139 |
| 2007/0260178 | A1 * | 11/2007 | Skerven | A61B 17/3478 604/164.01 |
| 2008/0269558 | A1 * | 10/2008 | Yahagi | A61B 18/1477 600/106 |
| 2008/0306334 | A1 * | 12/2008 | Okada | A61B 18/1492 30/151 |
| 2009/0048487 | A1 * | 2/2009 | Yanuma | A61B 18/1492 600/128 |
| 2009/0069802 | A1 * | 3/2009 | Garito | A61B 18/14 606/49 |
| 2010/0125272 | A1 * | 5/2010 | Scopton | A61B 17/3478 606/41 |
| 2010/0317997 | A1 * | 12/2010 | Hibner | A61B 10/0275 600/567 |
| 2011/0046513 | A1 * | 2/2011 | Hibner | A61B 10/0275 600/567 |
| 2011/0105944 | A1 * | 5/2011 | Ohnishi | A61B 10/0266 600/566 |
| 2012/0109007 | A1 * | 5/2012 | Rhad | A61B 10/0096 600/567 |
| 2012/0109277 | A1 * | 5/2012 | Lepulu | A61M 25/0082 606/191 |
| 2012/0172667 | A1 * | 7/2012 | Takeuchi | A61B 1/0055 600/140 |
| 2012/0265095 | A1 * | 10/2012 | Fiebig | A61B 10/0275 600/567 |
| 2013/0345704 | A1 * | 12/2013 | Palmer | A61B 18/148 606/41 |
| 2014/0288554 | A1 * | 9/2014 | Okada | A61B 18/14 606/45 |
| 2014/0371626 | A1 * | 12/2014 | Hibner | A61B 10/0096 600/567 |
| 2015/0157192 | A1 * | 6/2015 | Piskun | A61B 1/00085 600/114 |
| 2015/0272556 | A1 * | 10/2015 | Lee | A61M 25/0136 600/566 |
| 2016/0220301 | A1 * | 8/2016 | Yamamoto | A61B 18/14 |
| 2016/0361084 | A1 * | 12/2016 | Weisenburgh, II | A61B 18/1482 |
| 2017/0150871 | A1 * | 6/2017 | Arai | A61B 1/05 |
| 2017/0311936 | A1 * | 11/2017 | Suzuki | A61B 10/0275 |
| 2018/0303509 | A1 * | 10/2018 | Germain | A61B 17/16 |
| 2018/0368909 | A1 * | 12/2018 | Zhou | A61B 1/00087 |

FOREIGN PATENT DOCUMENTS

| | | | | |
|---|---|---|---|---|
| JP | 2011-206228 A | | 10/2011 | |
| KR | 101310371 B1 | * | 9/2013 | ......... A61B 17/3203 |
| KR | 10-1328473 B1 | | 11/2013 | |
| KR | 20-2014-0005806 U | | 11/2014 | |
| KR | 20180016117 A | * | 2/2018 | ............... A61B 1/00 |
| PT | 1011494 E | * | 1/2007 | ....... A61B 17/32002 |
| WO | WO-9829043 A1 | * | 7/1998 | ............. A61B 17/221 |
| WO | WO-2012115363 A2 | * | 8/2012 | ....... A61B 17/32023 |
| WO | WO-2014196746 A1 | * | 12/2014 | ............ A61B 17/722 |
| WO | WO-2016018457 A1 | * | 2/2016 | ....... A61B 17/32002 |

\* cited by examiner

ENDOSCOPE HYBRID KNIFE

TECHNICAL FIELD

The present disclosure relates to an endoscope hybrid knife, and more particularly, to an endoscope hybrid knife, which may include different kinds of knives to easily dissect and resect the submucosal tissue in the vertical and horizontal directions even without the replacement of the knives.

BACKGROUND ART

Recently, the so-called endoscopic submucosal dissection (ESD) is widely performed to insert a high frequency knife, or the like, which is a kind of a electric scalpel, to ablate a lesion site by using an endoscope without laparotomy of malignant and benign lesion sites in the submucosa of biological body cavities such as esophagus, stomach, small intestine, and large intestine.

The conventional endoscope high frequency knife has a thin and long insertion part and an operation part for operating it, and the insertion part is inserted into the body through the interior of the channel of the endoscope. The insertion part has a flexible tube and an operation wire movably inserted into the flexible tube in the axial direction, and a knife part extending in the axial direction is installed on the front end portion of the operation wire. The operation part may be connected to the proximal end portion of the insertion part to move the operation wire in the axial direction by an operation handle installed at one end thereof. The high frequency current passes through the operation wire to the knife part.

During the procedure through the high frequency knife, the operation handle may be operated to move the operation wire and the knife part connected thereto from the interior of the flexible tube to a position protruded to the exterior of the flexible tube. As described above, it is possible to allow the high frequency current to flow from the position where the procedure is required to the knife part protruded to the exterior of the flexible tube, thereby cauterization-dissecting the biological tissue contacting the knife part.

Typically, the knife part is provided with an insulating tip, for example, a ceramic tip, and thus, it is possible to dissect the submucosal tissue along the horizontal direction by the insulating tip knife, thereby preventing perforation. However, generally, there is a problem in that the smooth dissection cannot be made due to the ceramic tip, in particular, the marking and the vertical directional cutting is difficult to do.

At this time, a non-insulating knife such as a hook knife having the knife part of a non-insulating material may be provided and replaced to dissect the submucosal tissue more quickly.

However, there is a problem in that since the non-insulating knife as described above requires a higher precision due to the risk of perforation and as described above, the endoscopy treatment device, that is, a high frequency knife, needs to be replaced for the submucosal ablation, an operation of inserting the non-insulating knife into and withdrawing it from the body again should be repeated through the interior of the channel of the endoscope, thereby taking a long time and being troublesome.

DETAILED DESCRIPTION OF INVENTION

Technical Problem

The present disclosure is intended to solve the above problems, and an object of the present disclosure is to provide an endoscope hybrid knife, which may include different kinds of knives to easily dissect and resect the submucosal tissue in the vertical and horizontal directions even without the replacement of the knives.

Technical Solution

The present disclosure for achieving the object provides an endoscope hybrid knife including a handle part having a hollow, and having an opening connected to the hollow formed at one side thereof, first and second handle sliders coupled to the outer circumferential surface of the handle part to be slidable forward and backward along the longitudinal direction thereof, a pipe disposed at the hollow of the handle part and connected to the first handle slider to be movable integrally with the first handle slider, a second knife disposed to pass through the pipe and connected to the second handle slider to be movable integrally with the second handle slider, a fluid injection part coupled to one end of the handle part, and configured to inject fluid therein, an inner tube connected to one end of the fluid injection part and having the pipe disposed therein, a first knife coupled to the end of the pipe, and an insulating tip coupled to the end of the first knife, and the first knife and the second knife are slidable independently of each other.

The second knife may be protruded to the outside of the first knife or accommodated in the first knife.

Further, the endoscope hybrid knife may further include a first stopper coupled to the second knife, and the first stopper may contact the first knife and limit the length of the second knife protruded to the front end of the first knife.

Further, the endoscope hybrid knife may further include a second stopper coupled to the interior of the pipe, and the second stopper may contact the first stopper and limit the length of the second knife inserted into the pipe.

Further, the endoscope hybrid knife may further include a discharge guide inserted into the end portion of the inner tube, and formed with a fluid discharge hole through which the first knife passes.

The discharge guide may include a plurality of third stoppers disposed around the fluid discharge hole along its circumference, and the third stopper may contact the pipe and limit the length of the first knife protruded to the front end of the inner tube.

Further, the endoscope hybrid knife may further include an inner coil formed to be wound around the inner circumferential surface of the inner tube.

The fluid injected through the fluid injection part may flow through a space between the inner coil and the pipe to be discharged to the front end of the first knife through the fluid discharge hole.

The second handle slider may be coupled to the handle part in a ratchet structure.

Further, the endoscope hybrid knife may further include an electrode part connected to the pipe through the opening of the handle part.

A portion of the pipe may be formed of a bendable flexible tube.

The insulating tip may be formed of a ceramic head formed to be protruded to the outside of the radial direction of the first knife.

The second knife may be protruded from the front end of the first knife within a range of 1 mm or more and 3 mm or less.

The first knife may be protruded from the front end of the inner tube within a range of 4 mm or more and 6 mm or less.

Further, the endoscope hybrid knife may further include an outer tube coupled to one end of the fluid injection part and formed to surround a portion of the inner tube.

The outer tube may be formed of a Teflon tube.

A handle ring may be formed at the end of the handle part.

Advantageous Effects

According to the endoscope hybrid knife of the present disclosure, it is possible to easily dissect and resect the submucosal tissue in the vertical and horizontal directions even without the replacement if the hybrid knife is inserted through the interior of the endoscope channel once.

Specifically, it is possible to stably perform the cutting in the horizontal direction by the first knife including the insulating tip, and to easily perform the marking and the vertical directional cutting when using the second knife by protruding it to the exterior of the first knife.

As described above, it is not necessary to repeat the operation of inserting the knife into and withdrawing it from the body again for the replacement through the interior of the channel of the endoscope, thereby shortening the procedure time, and being safer.

It should be understood that the effects of the present disclosure are not limited to the above-described effects, and include all the effects inferred from the configuration of the disclosure described in the detailed description or claims of the present disclosure.

BEST MODE

Figure 1:
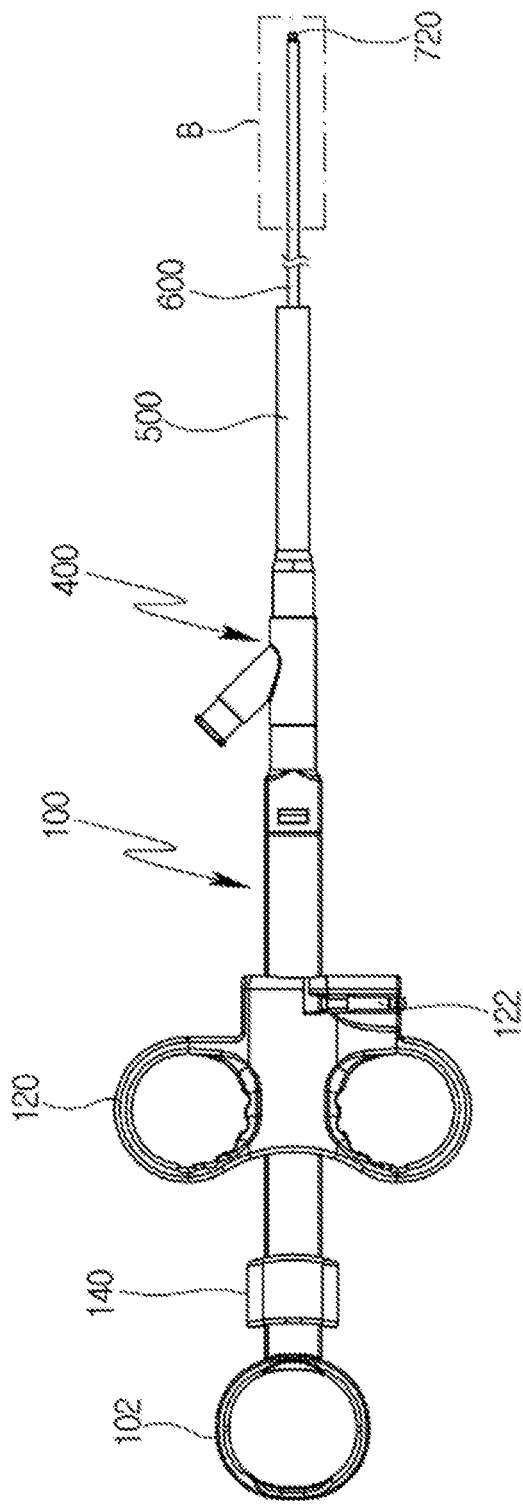
FIG. 1 is a front diagram illustrating an endoscope hybrid knife according to an embodiment of the present disclosure.

Hereinafter, preferred embodiments of an endoscope hybrid knife according to the present disclosure will be described with reference to FIGS. 1 to 9.

Further, terms to be described later are terms defined considering functions in the present disclosure, which may vary according to intentions or customs of users or operators, and the following embodiments do not limit the scope of the present disclosure but are merely illustrative of the components recited in the claims of the present disclosure.

In order to clearly describe the present disclosure, parts irrelevant to the description are omitted, and the same or like elements are denoted by the same reference numerals throughout the specification. Throughout the specification, when a part is said to "include" a certain component, it means that it may further include other components without excluding the other components unless specially stated otherwise.

Figure 2:
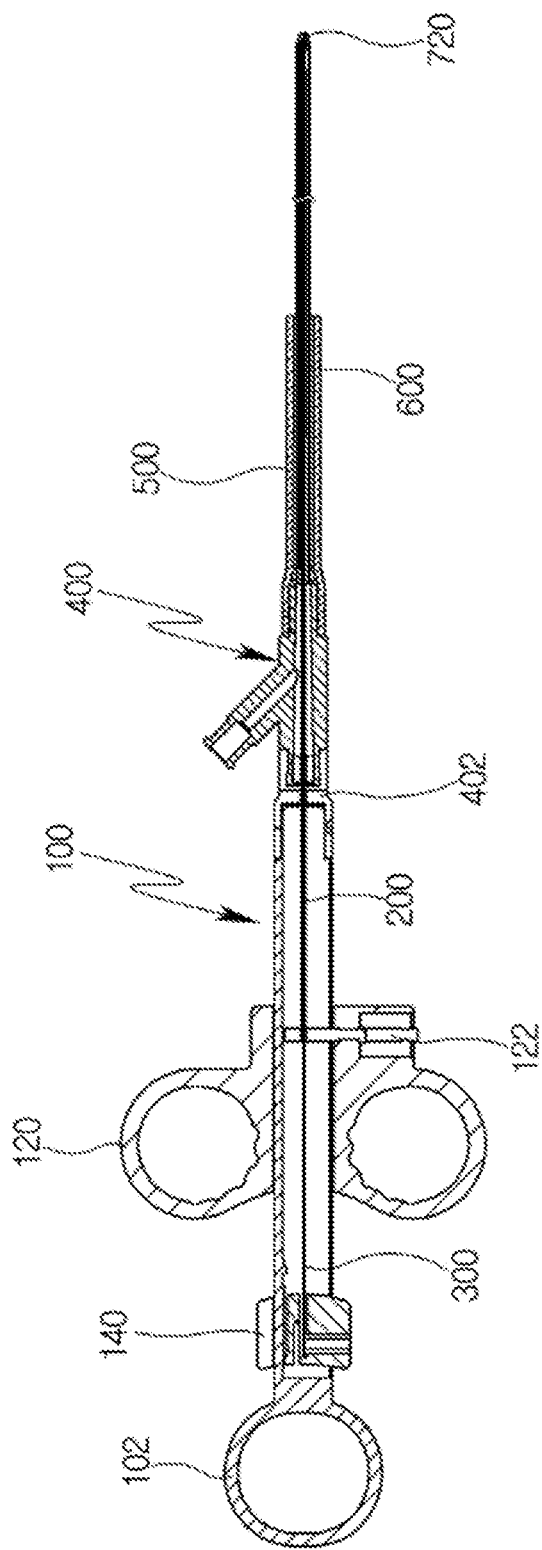
FIG. 2 is a cross-sectional diagram of FIG. 1.
Figure 3:
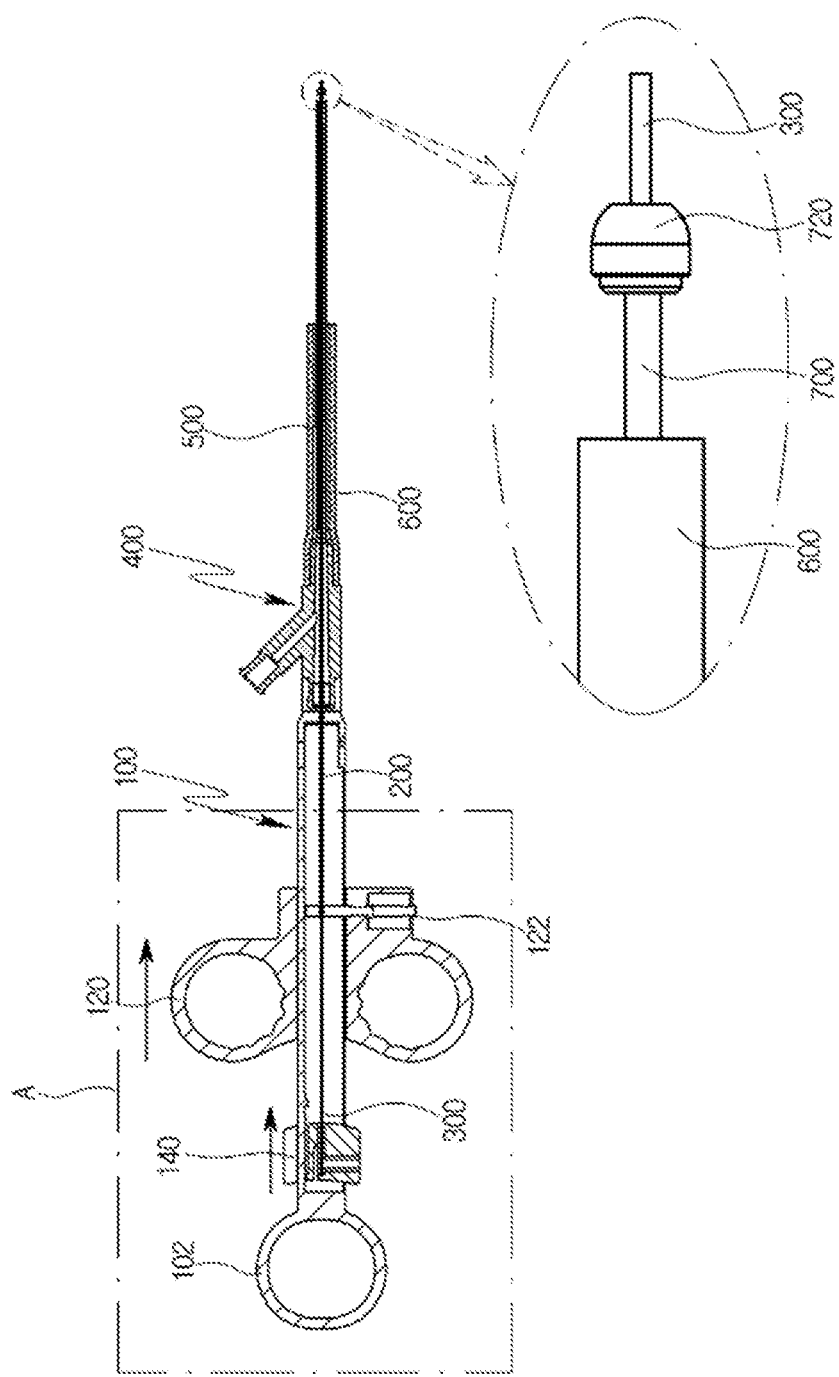
FIG. 3 is a cross-sectional diagram illustrating another state of FIG. 2.
Figure 4:
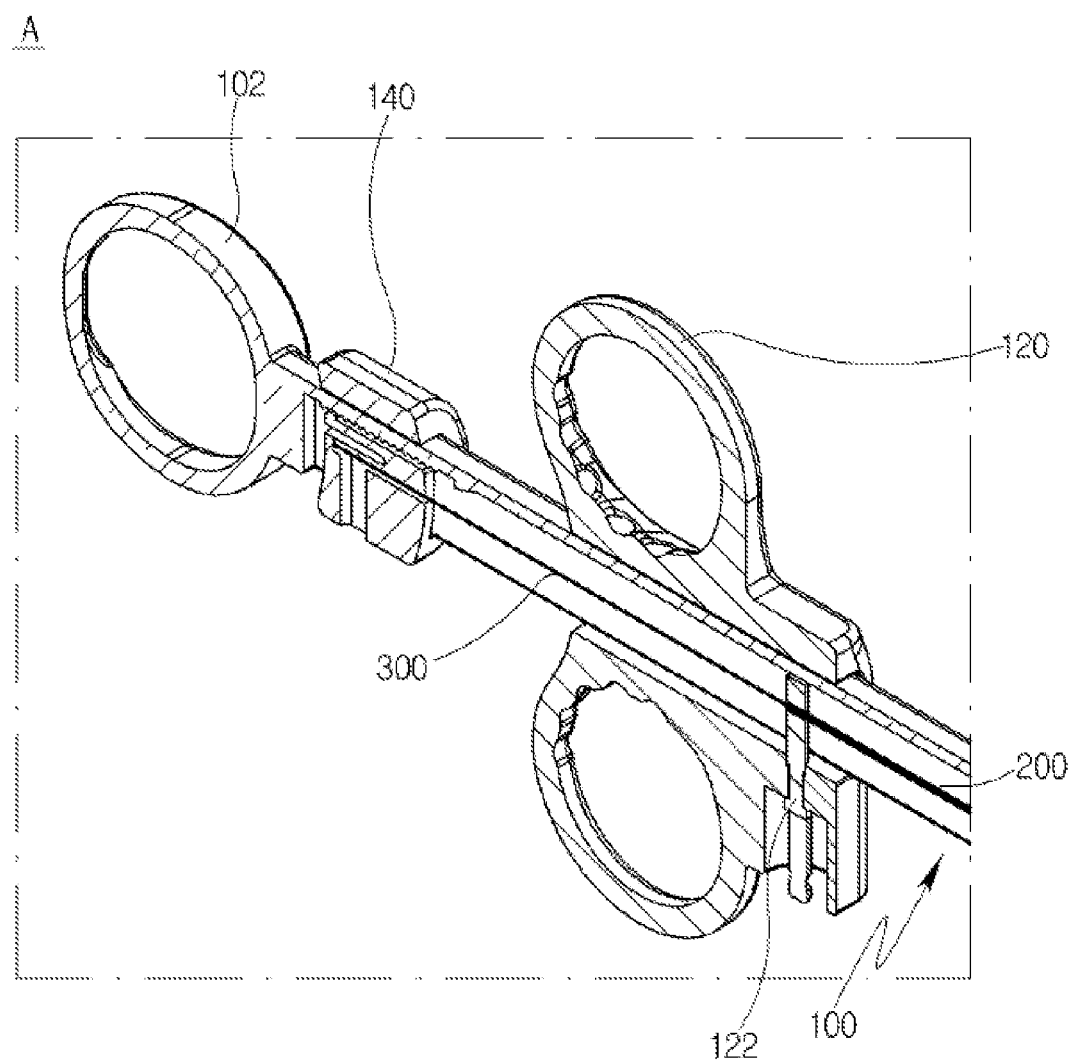
FIG. 4 is an enlarged perspective diagram of a portion A in FIG. 3.
Figure 5:
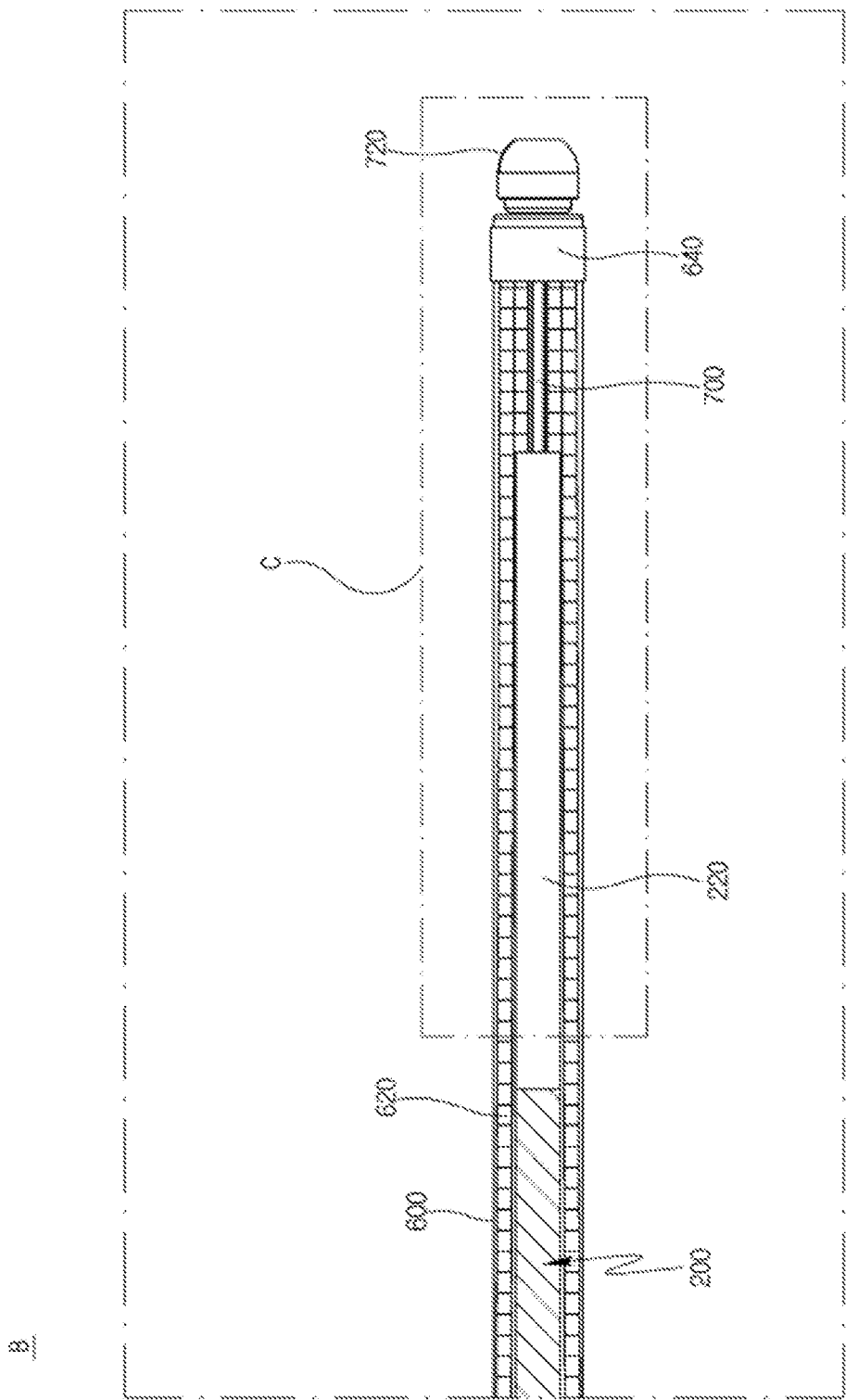
FIG. 5 is a partial cross-sectional diagram of a portion B in FIG. 1.
Figure 6:
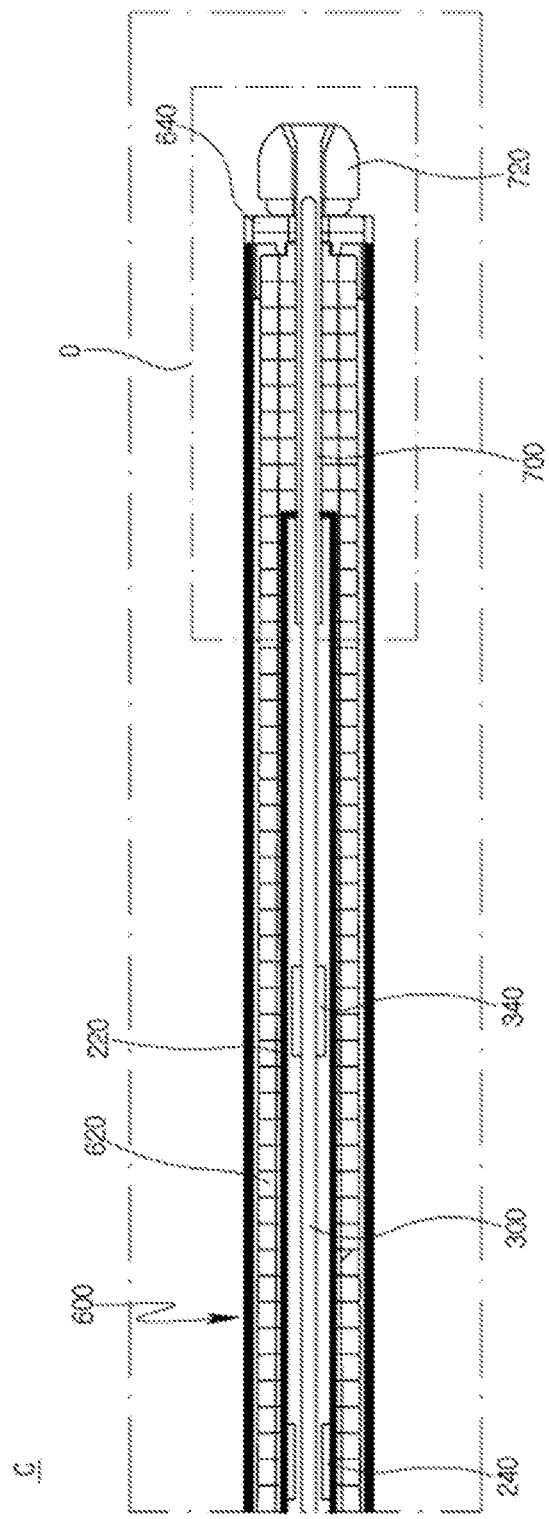
FIG. 6 is an enlarged cross-sectional diagram of a portion C in FIG. 5.
Figure 7:
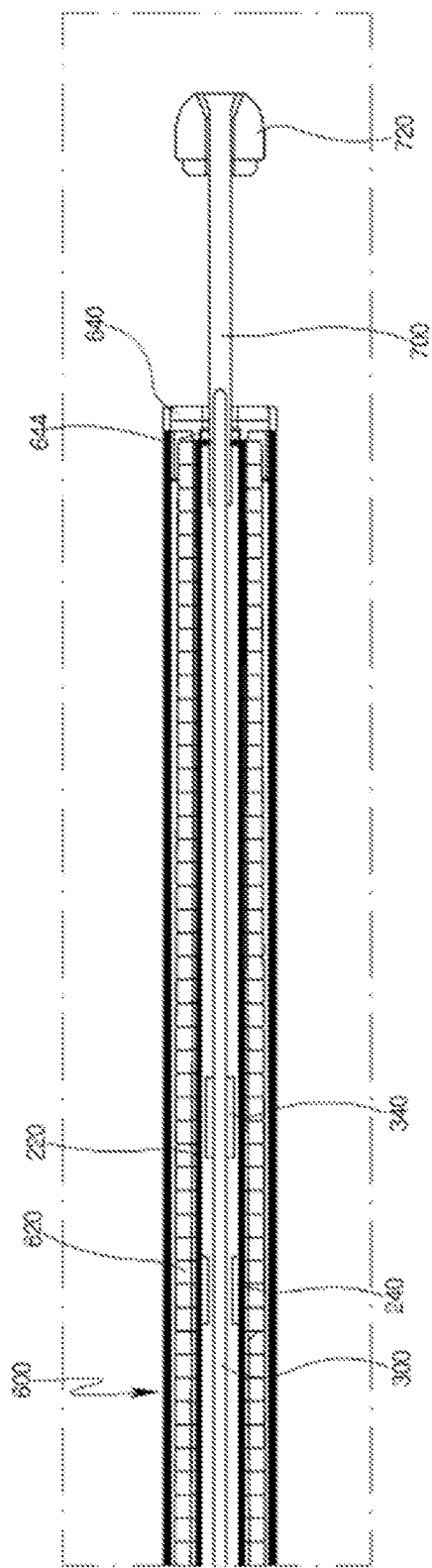
FIG. 7 is a cross-sectional diagram illustrating another state of FIG. 6.
Figure 8:
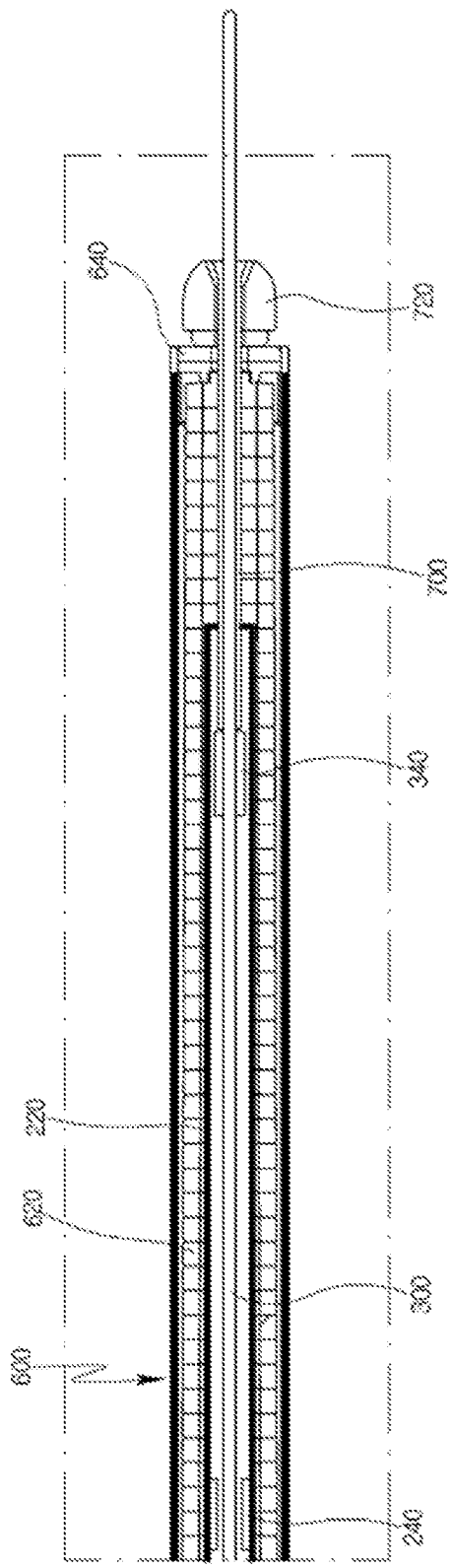
FIG. 8 is a cross-sectional diagram illustrating still another state of FIG. 6.
Figure 9:
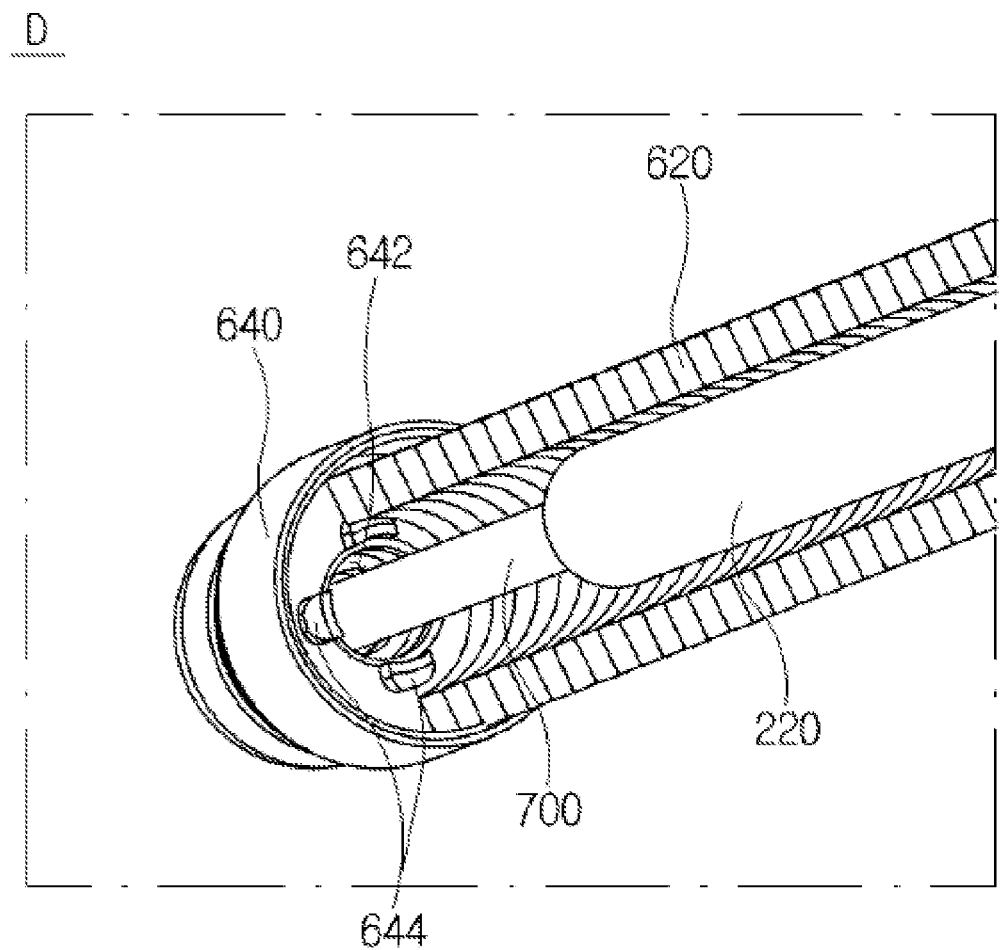
FIG. 9 is a perspective diagram excluding an inner tube in a portion D in FIG. 6.

FIG. 1 is a front diagram illustrating an endoscope hybrid knife according to an embodiment of the present disclosure, FIG. 2 is a cross-sectional diagram of FIG. 1, FIG. 3 is a cross-sectional diagram illustrating another state of FIG. 2, FIG. 4 is an enlarged perspective diagram of a portion A in FIG. 3, FIG. 5 is a partial cross-sectional diagram of a portion B in FIG. 1, FIG. 6 is an enlarged cross-sectional diagram of a portion C in FIG. 5, FIG. 7 is a cross-sectional diagram illustrating another state of FIG. 6, FIG. 8 is a cross-sectional diagram illustrating still another state of FIG. 6, and FIG. 9 is a perspective diagram excluding an inner tube in a portion D in FIG. 6.

Hereinafter, a structure of the endoscope hybrid knife according to an embodiment of the present disclosure will be described with reference to the drawings.

For reference, in the following description of the endoscope hybrid knife according to the present disclosure, it will be described that the side where the operation part for operating outside the body is positioned is defined as the rear, and the side where the insertion part connected to the operation part to be inserted into the body is positioned is defined as the front.

The endoscope hybrid knife according to the present disclosure may be used for marking and dissecting the lesion site by being inserted into the body, and used for the Endoscopic Submucosal Dissection (ESD), or used for removing early gastric cancer, adenoma, or the like generated in esophagus, stomach, large intestine, and the like.

As illustrated in FIGS. 1 to 3, the endoscope hybrid knife according to an embodiment of the present disclosure may be composed of an insertion part inserted into the body and an operation part coupled to the insertion part for operating it, and may include a handle part 100, a first handle slider 120, a second handle slider 140, a pipe 200, a second knife 300, a fluid injection part 400, an outer tube 500, an inner tube 600, and a first knife 700.

The handle part 100 forms the axis of the operation part, has a shape of a pillar having a hollow therein, and has an opening connected to the hollow formed at one side thereof. The cross section of the handle part 100 may have any shape, such as a circle, a rectangle, or a triangle, but in the present embodiment, it is formed in the cross section of a rectangle, and an opening is formed on one surface of the four surfaces of the rectangle along the longitudinal direction thereof.

A handle ring 102 may be formed at the end of the handle part 100, and the handle ring 102 may have any shape such as a circular ring and a rectangular ring. The operation is performed by inserting the thumb into the handle ring 102, thereby enabling easy operation.

The first handle slider 120 and the second handle slider 140 are coupled to the outer circumferential surface of the handle part 100 to be slidable forward and backward along the longitudinal direction of the handle part. That is, the handle part 100 passes through the first and second handle sliders 120, 140, and the first handle slider 120 and the second handle slider 140 are slidable independently, respectively, and in the present embodiment, the second handle slider 140 is positioned behind the first handle slider 120.

At this time, specifically describing the shape of the first handle slider 120, based on the case where the thumb has been inserted into the handle ring 102, the rings into which the index finger and the middle finger may be inserted are provided at the upper side and the lower side thereof, respectively. Further, the second handle slider 140 may be formed in a pillar shape to be gripped and moved by hand. However, the present disclosure is not limited thereto and the shapes of the first handle slider 120 and the second handle slider 140 may be formed variously.

Further, a plurality of grooves for fixing and organizing a tube, an electrode wire, and the like in the storage state after the procedure may also be formed at one side of the first handle slider 120.

The first handle slider 120 is connected with the pipe 200 to be movable integrally therewith, and the second handle slider 140 is connected with the second knife 300 to be movable integrally therewith. Therefore, the pipe 200 and the second knife 300 are disposed in the hollow of the handle part 100, and the second knife 300 is disposed to pass through the pipe 200.

Since the first handle slider 120 and the second handle slider 140 are slidable independently, respectively, the pipe 200 and the second knife 300 are slidable independently of each other, and as described in detail below, the second knife 300 may be protruded to the exterior of the first knife 700 or accommodated therein. At this time, considering safety during the procedure, if the first knife 700 is protruded, the second knife 300 may maintain the accommodated state.

The forward and backward movement of the first handle slider 120 may be delivered to the first knife 700 to be described later through the pipe 200. The second knife 300 may be made of a metal such as stainless steel, and is preferably formed in a shape of a strand such as a wire having flexibility and excellent delivery force.

At this time, a reinforcing part surrounding the second knife 300 by a certain length may be formed so that the second knife 300 moves while maintaining the straightness without being bent, even when receiving a force at the forward and backward movement of the second handle slider 140.

Further, the electrode part 122 is a place where a high frequency connection line, or the like is connected to receive a high frequency from a high frequency generator used for a separate medical use, and the electrode part 122 is connected to the pipe 200 through the opening of the handle part 100 from one side of the first handle slider 120.

Therefore, if a high frequency current is applied through the electrode part 122, the high frequency current is delivered to the first knife 700 of the end to be described later through the pipe 200, and the high frequency current may also be delivered to the second knife 300 due to the interference with the pipe 200.

The fluid injection part 400 is a part coupled to one end of the front of the handle part 100, and for injecting fluid therein. To this end, the fluid injection part 400 may include an injection tube in the form of a protruded tube for receiving a fluid such as water or saline from the exterior to the interior thereof, and the fluid thus injected may flow up to the front of the inner tube 600 to be discharged as described later.

The fluid injection part 400 may be connected with the handle part 100 by a separate connector 402, and have a hollow formed therein, such that the fluid may flow therethrough as well as the pipe 200 may be disposed.

The outer tube 500 may be coupled to the front of the fluid injection part 400, and the inner tube 600 is disposed to pass through the outer tube 500. That is, the inner tube 600 is formed to be connected to one end of the fluid injection part 400 or to extend from the interior of the fluid injection part 400 to be disposed in the hollow of the outer tube 500.

As described above, the outer tube 500 and the inner tube 600 may be fixed to the fluid injection part 400, and the outer tube 500 may be made of a material having more rigidity than that of the inner tube 600, thereby firmly maintaining the inner tube 600 and enabling buckling prevention.

The outer tube 500 may be formed of a Teflon tube, and the inner tube 600 may be preferably formed in a tubular shape having insulation and flexibility made of a resin or the like.

Further, as illustrated in FIGS. 5 to 8, an inner coil 620 may be formed to be wound around the inner circumferential surface of the inner tube 600.

Therefore, the pipe 200 may be disposed inside the inner coil 620, and at this time, a space may be formed between the inner coil 620 and the pipe 200 to allow fluid to flow therein.

As illustrated in FIGS. 2 and 3, the pipe 200 is connected to the first handle slider 120 to be disposed to pass through the interiors of the handle part 100, the fluid injection part 400, the outer tube 500, and the inner tube 600. Since the pipe 200 is connected to the first handle slider 120 to be integrally moved, the pipe 200 may be moved forward and backward by sliding the first handle slider 120 forward and backward.

At this time, the end of the pipe 200 is coupled to the first knife 700 for dissecting and resecting the submucosal tissue to be integrally movable forward and backward. In the present embodiment, the first knife 700 is coupled to the interior of the end of the front of the pipe 200, and has a hollow formed therein, such that the second knife 300 may pass through the first knife 700 and move forward and backward.

Further, an insulating tip may be coupled to the end of the first knife 700. In the present embodiment, the insulating tip is formed of a ceramic head 720 formed to be protruded to the outside of the radial direction of the first knife 700.

The ceramic head 720 has a rounded shape forward, and has a hollow formed in the center thereof so that the end of the first knife 700 is disposed through the hollow, and therefore, the ceramic head 720 is coupled while surrounding the end of the first knife 700.

Therefore, the ceramic head 720 may serve to protect at the dissection through the first knife 700, thereby preventing perforation caused by the contact of the front surface portion of the first knife 700 with the normal tissue. Further, it is possible to easily perform the horizontal directional cutting by using the first knife 700, and to safely move the endoscope hybrid knife according to the present disclosure through the insulating ceramic head 720 when being inserted into or withdrawn it from the body through the interior of the endoscope channel.

Further, since the second knife 300 is disposed to pass through the interior of the pipe 200, the second knife 300 is likewise connected to the second handle slider 140 to be disposed to pass through the interiors of the handle part 100, the fluid injection part 400, the outer tube 500, and the inner tube 600. Since the second knife 300 is connected to the second handle slider 140 to move integrally, the second knife 300 may move forward and backward by sliding the second handle slider 140 forward and backward.

At this time, as illustrated in FIG. 4, in order to prevent the second knife 300 from moving together by the friction due to the interference when the pipe 200 moves forward and backward, the second handle slider 140 may be coupled to the handle part 100 in a ratchet structure. Here, the ratchet structure is one coupled to have a tooth of the sawtooth shape. Therefore, since the second handle slider 140 does not move with respect to the handle part 100 unless a force of a certain level is applied, the second knife 300 may be fixed even in the case where the pipe 200 moves.

Unlike the first knife 700, since the insulating tip is not coupled to the second knife 300, the marking and the vertical directional cutting of the lesion are easy to do. However, since the second knife 300 does not include an insulator so there is a risk of perforation when contacting the normal tissue, the second knife 300 is accommodated in the interior hollow of the first knife 700, as illustrated in FIGS. 6 and 7, during the insertion or the horizontal directional cutting of the endoscope hybrid knife according to the present disclosure. As described above, only when the marking and the vertical directional cutting of the lesion are required, as illustrated in FIG. 8, the second handle slider 140 is moved forward to protrude the second knife 300 from the front of the first knife 700, thereby performing safe and easy procedure.

Specifically, according to the procedure order, as illustrated in FIG. 8, the second knife 300 may be protruded from the inside of the first knife 700 to perform the marking and the vertical directional cutting of the lesion to be resected. Subsequently, as illustrated in FIG. 7, the second knife 300 is accommodated inside the first knife 700, and the horizontal directional cutting may be stably performed by the first knife 700 including the insulating tip.

In the present embodiment, the end of the second knife 300 has been formed in the straight line, but it is not limited thereto and may also be formed by bending at a certain angle.

The endoscope hybrid knife may further include a first stopper 340 coupled to the second knife 300 in order to limit the length of the second knife 300 protruded to the front end of the first knife 700.

As illustrated in FIG. 8, as the second knife 300 is moved forward together with the second handle slider 140, the first stopper 340 may contact one end portion of the first knife 700, thereby limiting the length of the second knife 300 protruded to the front end of the first knife 700.

Since the risk of perforation increases if the second knife 300 is protruded from the first knife 700 too much, in the present embodiment, the second knife 300 may be formed to be protruded from the front end of the first knife 700 within a range of 1 mm or more and 3 mm or less.

In the case of winding the endoscope hybrid high frequency product according to the present disclosure by two wheels or more, in particular, winding the inner tube 600 by two wheels or more during the procedure, there may appear the phenomenon in which the second knife 300 is completely accommodated to the rear side of the pipe 200 to make it difficult to be discharged to the front thereof. In order to prevent it, the endoscope hybrid knife may further include a second stopper 240 coupled to the interior of the pipe 200.

As illustrated in FIG. 6, when the second knife 300 is moved backward together with the second handle slider 140, the second stopper 240 may contact the first stopper 340, thereby limiting the length of the second knife 300 inserted into the pipe 200.

Further, as illustrated in FIG. 9, a discharge guide 640 is inserted into the end portion of the inner tube 600, and a fluid discharge hole 642 through which the first knife 700 passes is formed in the discharge guide 640.

The fluid discharge hole 642 is preferably formed in the center of the discharge guide 640, the size of the diameter of the fluid discharge hole 642 is formed larger than the diameter of the first knife 700 so that the first knife 700 may pass through, and formed smaller than the diameter of the pipe 200 so that the pipe 200 should be formed in the size that may not pass through.

Therefore, the fluid injected through the fluid injection part 400 may flow through the space between the inner coil 620 and the pipe 200 to be discharged to the front end of the first knife 700 through the fluid discharge hole 642. Specifically, the fluid may be discharged to the clearance between the pipe 200 and the discharge guide 640 generated by the pipe 200 contacting a third stopper 644 to be described later.

At this time, the discharge of the fluid during the procedure may be mainly made in a state where the first knife 700 has been protruded to the front end of the inner tube 600.

The discharge guide 640 may include a plurality of third stoppers 644 disposed along its circumference around the fluid discharge hole 642, and the third stopper 644 may be formed to be protruded toward the pipe 200 side. The plurality of third stoppers 644 are preferably disposed at certain intervals, and in the present embodiment, the plurality of third stoppers 644 are formed of four teeth having 90° to each other along the circumference of the fluid discharge hole 642.

As illustrated in FIG. 7, as the pipe 200 is moved forward together with the first handle slider 120, the third stopper 644 may contact one end portion of the pipe 200, thereby limiting the length of the first knife 700 coupled to the pipe 200 protruded to the front end of the inner tube 600.

In the present embodiment, the first knife 700 may be formed to be protruded from the front end of the inner tube 600 within a range of 4 mm or more and 6 mm or less.

As illustrated in FIG. 5, a portion of the pipe 200 may be formed of a bendable flexible tube 220. This is for improving a problem in that there occurs the case where the hybrid knife according to the present disclosure is bent by a certain angle when entering the body through the endoscope channel, and at this time, the bending force is small and therefore, the discharged length of the first knife 700 is not constant or the first knife 700 is not discharged.

Therefore, a portion of the pipe 200, in particular, a portion of the front of the pipe 200 may be formed of the flexible tube 220 having good straightness and a good bending force, and in the present embodiment, about 20 cm of the front of the pipe 200 is formed of the flexible tube 220.

However, the present disclosure is not limited thereto, and the length may be changed within a certain range according to the specification of the endoscope and the preference of the operator, and preferably, formed in the size of about 20 to 50 cm.

As a result, the second stopper 240 may be coupled to the interior of the flexible tube 220, and it is natural that the first knife 700 may be coupled to one end portion of the flexible tube 220.

The present disclosure is not limited to the above-described specific embodiments and descriptions, and various modifications may be made by those skilled in the art to which the present disclosure pertains without departing from the gist of the present disclosure as claimed in the claims, and such modifications are within the protection scope of the present disclosure.

INDUSTRIAL APPLICABILITY

The present disclosure relates to an endoscope hybrid knife, and more particularly, to an endoscope hybrid knife, which may include different kinds of knives to easily dissect and resect the submucosal tissue in the vertical and horizontal directions even without the replacement of the knives.

What is claimed is:

1. An endoscope hybrid knife, comprising:
   a handle having a shape of a pillar having a hollow, and having an opening connected to the hollow formed at one side thereof;
   first and second handle sliders coupled to an outer circumferential surface of the handle to be slidable forward and backward along a longitudinal direction of the handle;
   a pipe disposed in the hollow of the handle and connected to the first handle slider to be movable integrally with the first handle slider;
   a first knife coupled to an end of the pipe;
   an insulating tip coupled to an end of the first knife;
   a second knife disposed to pass through the pipe and connected to the second handle slider to be movable integrally with the second handle slider, the second knife being slidable with respect to the pipe in a longitudinal direction of the pipe;
   a fluid injection tube coupled to one end of the handle, and configured to inject fluid therein;
   an inner tube connected to one end of the fluid injection tube and having the pipe disposed therein; and
   a discharge guide coupled to an end portion of the inner tube,
   wherein the discharge guide has a fluid discharge hole which has a circular shape with a diameter greater than a diameter of the first knife to allow the first knife to move through the fluid discharge hole, and the discharge guide includes a plurality of stoppers disposed around the fluid discharge hole along a circumference thereof,
   wherein the fluid injected through the fluid injection tube flows through a space between the inner tube and the pipe to be discharged to a front end of the first knife through a gap between the fluid discharge hole and the first knife,
   wherein both the first knife and the second knife are slidable with respect to the inner tube in a longitudinal direction of the inner tube and slidable independently of each other.

2. The endoscope hybrid knife of claim 1,
   wherein the second knife is configured to be protruded out from the first knife or accommodated in the first knife.

3. The endoscope hybrid knife of claim 2, further comprising a first stopper coupled to the second knife,
   wherein the first stopper is configured to contact the first knife so as to limit a length of the second knife protruded to the front end of the first knife.

4. The endoscope hybrid knife of claim 3, further comprising a second stopper coupled to an interior of the pipe,
   wherein the second stopper is configured to contact the first stopper so as to limit a length of the second knife inserted into the pipe.

5. The endoscope hybrid knife of claim 1,
   wherein the plurality of stoppers are configured to contact the pipe so as to limit a length of the first knife protruded to a front end of the inner tube.

6. The endoscope hybrid knife of claim 5, further comprising an inner coil wound around an inner circumferential surface of the inner tube.

7. The endoscope hybrid knife of claim 1, further comprising an electrode connected to the pipe through an opening of the handle.

8. The endoscope hybrid knife of claim 1,
   wherein a portion of the pipe is formed of a bendable flexible tube.

9. The endoscope hybrid knife of claim 1,
   wherein the insulating tip is formed of a ceramic head protruding in a radial direction of the first knife.

10. The endoscope hybrid knife of claim 3,
    wherein the second knife is configured to be protruded from the front end of the first knife within a range of 1 mm or more and 3 mm or less.

11. The endoscope hybrid knife of claim 5, wherein the first knife is configured to be protruded from the front end of the inner tube within a range of 4 mm or more and 6 mm or less.

12. The endoscope hybrid knife of claim 1, further comprising an outer tube coupled to one end of the fluid injection tube and surrounding a portion of the inner tube.

13. The endoscope hybrid knife of claim 12,
    wherein the outer tube includes a polytetrafluoroethylene tube.

14. The endoscope hybrid knife of claim 1,
    wherein the handle includes a handle ring formed at an end thereof.

15. The endoscope hybrid knife of claim 1,
    wherein the first knife is configured to be protruded from the inner tube by forward movement of the first slider, and the second knife is configured to be protruded from the first knife by forward movement of the second slider.

16. The endoscope hybrid knife of claim 1,
    wherein the second handle slider is coupled to the handle in such a way that inner surface of the handle in the shape of the pillar is in contact with the second handle slider and teeth are formed in a longitudinal direction of the handle at least partially along the inner surface of the handle that is in contact with the second handle slider so as for the second handle slider not to move with respect to the handle unless a force exceeding a predetermined level is applied.

* * * * *